(12) United States Patent
Choi et al.

(10) Patent No.: US 9,301,943 B2
(45) Date of Patent: Apr. 5, 2016

(54) USE OF EUPATILIN

(71) Applicant: UNIVERSITY-INDUSTRY COOPERATION GROUP OF KYUNG HEE UNIVERSITY, Yongin-si, Gyeonggi-do (KR)

(72) Inventors: Jung-Hye Choi, Seoul (KR); Kyung-Tae Lee, Seoul (KR); Ji-Hyun Kim, Seoul (KR); Nam-In Baek, Hwaseong-si (KR)

(73) Assignee: UNIVERSITY-INDUSTRY COOPERATION GROUP OF KYUNG HEE UNIVERSITY, Yongin-Si, Gyeonggi-Do (KR)

( * ) Notice: Subject to any disclaimer, the term of this patent is extended or adjusted under 35 U.S.C. 154(b) by 0 days.

(21) Appl. No.: 14/348,453

(22) PCT Filed: Sep. 27, 2012

(86) PCT No.: PCT/KR2012/007841
§ 371 (c)(1),
(2) Date: Mar. 28, 2014

(87) PCT Pub. No.: WO2013/048158
PCT Pub. Date: Apr. 4, 2013

(65) Prior Publication Data
US 2014/0288168 A1   Sep. 25, 2014

(30) Foreign Application Priority Data
Sep. 29, 2011   (KR) .................. 10-2011-0099349

(51) Int. Cl.
| A01N 43/16 | (2006.01) |
| A61K 31/35 | (2006.01) |
| A61K 31/352 | (2006.01) |
| A61K 31/366 | (2006.01) |

(52) U.S. Cl.
CPC ............. *A61K 31/352* (2013.01); *A61K 31/366* (2013.01)

(58) Field of Classification Search
None
See application file for complete search history.

(56) References Cited

U.S. PATENT DOCUMENTS

| 5,874,084 A | * | 2/1999 | Yng-Wong | .................. 424/740 |
| 2012/0277171 A1 | | 11/2012 | Silva Martinot | |

FOREIGN PATENT DOCUMENTS

| CN | 101518558 A | 9/2009 |
| KR | 2002-0090672 A | 12/2002 |
| KR | 10-0414453 B | 4/2004 |
| KR | 10-2006-0121997 A | 11/2006 |
| KR | 10-2006-0121998 A | 11/2006 |
| KR | 10-0742737 B1 | 7/2007 |
| KR | 2010097517 A | * 9/2010 |

OTHER PUBLICATIONS

Cho et al. (Food and Chemical Toxicology, Apr. 29, 2011, 49, 1737-1744).*
Kim et al. (KR2010097517; Published Sep. 3, 2010 English machine translation).*
Jong-Min Han et al. (2nd Korea Research Institute of Bioscience and Biotechnology (KRIBB) Post Festival, Nov. 12, 2008).*
Cho et al. (Food and Chemical Toxicology, 2011, 1737-1744).*
Menonote (Menopause.org, 2014, http://www.menopause.org/docs/for-women/mnflashes.pdf).*
Bonnie J. Deroo, et al. "Estrogen receptors and human disease" J Clin Invest. vol. 116, No. 3, pp. 561-570 (Mar. 2006).
Jacques E. Rossouw, et al. "Risks and benefits of estrogen plus progestin in healthy postmenopausal women: principal results From the Women's Health Initiative randomized controlled trial". JAMA. vol. 288, No. 3, pp. 321-333, (Jul. 17, 2002).
Garnet L. Anderson, et al. "Effects of conjugated equine estrogen in postmenopausal women with hysterectomy: the Women's Health Initiative randomized controlled trial". JAMA. vol. 291, No. 14, pp. 1701-1712 (Apr. 14, 2004).
Sung-Won Min, et al., "Inhibitory effect of eupatilin and jaceosidin isolated from Artemisia princeps on carrageenan-induced inflammation in mice." Journal of Ethnopharmacology. vol. 125, pp. 497-500 (Jun. 6, 2009).
Lihuan Cao, et al. "Estrogen Receptor-beta Modulates Synthesis of Bone Matrix Proteins in Human Osteoblast-Like MG63 Cells." Journal of Cellular Biochemistry. vol. 89, pp. 152-164 (2003).
Sojin An, et al. "Eupatilin attenuates atherosclerosis and improves adipokine profiles in LDL recept-deficient mice", The Korean Society of Medical Crop Science, Spring Conference, pp. 168-169 (May 2008).
Jung-Noon Cho, et al. "Eupatilin, a dietary flavonoid, induces G2/M cell cycle arrest in human endometrial cancer cells" Food and Chemical Toxicology. vol. 49, pp. 1737-1744 (Apr. 29, 2011).
Su-Noh Ryu. Bioactive Constitiuents and Utilities of Ganghwayakssuk (Artemisia princeps Pamp.). Korean J. Intl. Agri. vol. 20, No. 4, pp. 308-314 (2008).

(Continued)

*Primary Examiner* — Dennis Heyer
*Assistant Examiner* — Daniel M Podgorski
(74) *Attorney, Agent, or Firm* — Novick, Kim & Lee, PLLC; Jae Youn Kim

(57) ABSTRACT

The present invention provides a medicinal and/or a food usage of eupatilin for treating, improving, and/or preventing at least one condition selected from bone disease, menopausal disorder, cardiovascular disease, neurodegenerative disease, or obesity. Advantages of the present invention includes little or no possibility of side effects such as cancer, and effective treatment, improvement, and/or prevention of the at least one condition selected from bone disease, menopausal disorder, cardiovascular disease, neurodegenerative disease, and obesity.

3 Claims, 3 Drawing Sheets

(56) References Cited

OTHER PUBLICATIONS

Sanghyun Lee et al. "Constituents from the Non-Polar Fraction of Artemisia apiacea" Arch Pharm Res. vol. 26, No. 11, pp. 902-905 (2003).

Sanghyun Lee et al. "Phytochemical Constituents from the Herba of Artemisia apiacea" Arch Pharm Res. vol. 25, No. 3, pp. 285-288 (2002).

Hiroko Shimomura et al. "The Chemical Components of Artemisia apiacea Hance. II. More Coumarins from the Flower Heads" Chem. Pharm. Bull. vol. 28, No. 1, pp. 347-348 (1980).

Kyoung Soon Kim et al. "Flavonol Galactosides from Artemisia apiacea" Natural Product Sciences, vol. 11, No. 1, pp. 10-12 (2005).

Sung-Jin Lee et al. "Apicin, A New Flavonoid from Artemisia apiacea" Bull. Korean Chem. Soc. vol. 27, No. 8, pp. 1225-1226 (2006).

The Healing Arc, "Beta-sitosterol Plus" http://www.thehealingarc.com/products-50.html, accessed on Apr. 24, 2015.

X. Zhou et al. "Chemical constituents in the roots of Lycium chinense Mill" (abstract only), http://www.ncbi.nlm.nih.gov/pubmed/9812695, accessed on Apr. 25, 2015.

WebMD, "Beta—Sitosterol" http://www.webmd.com/vitamins-supplements/ingredientmono-939-beta-sitosterol.aspx?activeingredientid=939&activeingredientname=beta-sitosterol, accessed on Apr. 25, 2015.

Cristiana Calicetic et al. "Potential Benefits of Berberine in the Management of Perimenopausal Syndrome" Oxidative Medicine and Cellular Longevity. vol. 2015, Article ID 723093, pp. 1-9 (2015).

Chan Co et al. "Analysis of berberine and total alkaloid content in cortex phellodendri by near infrared spectroscopy (NIRS) compared with high-performance liquid chromatography coupled with ultra-visible spectrometric detection." (abstract only) http://www.ncbi.nlm.nih.gov/pubmed/17512816, accessed on Apr. 25, 2015.

Jong-Min Han, et al. "Antioxidant property of eupatilin attenuates atherosclerosis and improves adipokine profiles in LDL receptor-deficient mice" 2nd Korea Research Institute of Bioscience and Biotechnology (KRIBB) Poster Festival. pp. 14 (Nov. 12, 2008).

\* cited by examiner

USE OF EUPATILIN

TECHNICAL FIELD

The present invention relates to novel use of eupatilin. More specifically, the present invention relates to use of eupatilin for the treatment, improvement or prevention of diseases or conditions which are caused by estrogen deficiency, such as bone diseases, menopausal disorders, cardiovascular diseases, neurodegenerative diseases and obesity.

BACKGROUND ART

It has been known that eupatilin can be used as a therapeutic agent for treating inflammatory bowel diseases (see Korean Patent No. 0414453). Eupatilin is also known as a substance which inhibits the activity of farnesyl transferase, an enzyme essential for the activation of ras oncogenes and angiogenesis and therefore can be used as an inhibitor of oncogene expression, an anti-cancer agent, an inhibitor of cancer metastasis, and a prophylactic agent for diabetic retinopathy and angiogenesis-related blindness following keratoplasty (see Korean Patent Application Publication No. 2002-0090672 A1). Further, with respect to anticancer action, eupatilin is also known to suppress the activity, invasion and migration of matrix metalloproteinase (MMP) to thereby inhibit the progression and metastasis of breast cancer (Korean Patent Application Publication No. 2006-0121998 A1).

Meanwhile, estrogen, a hormone secreted by the ovary, refers to a steroid compound having a C18 estrane nucleus. Typically, there are well known 3 types of estrogen: estrone (E1), estradiol (E2), and estriol (E3). Estrogen is known to exert a wide variety of effects in numerous organs, in addition to modulation of menstrual cycles. For example, it regulates production of cholesterol in the liver, maintains the bone density in bone, and plays a role in maturation of uterine walls. In recent years, estrogen has also been found to play an important role in neuronal cell viability and adipogenesis.

When there is a decline of the body's estrogen level due to ovarian failure at the menopause period, this leads to a decrease in the blood estrogen level, which may result in common menopausal disorders including hot flashes, sweating, insomnia, depression and headache, and bone diseases due to a decreased bone density. Moreover, a decrease in the body's estrogen level brings about an increased risk of plaque formation in the vascular system, resulting in development of cardiovascular diseases such as atherosclerosis, an increased incidence of neurodegenerative diseases such as Parkinson's disease and Alzheimer's disease caused by damage to the neuronal cells, and the occurrence of obesity resulting from deregulated adipogenesis (Deroo B J, Korach K S. (2006) "Estrogen receptors and human disease" J Clin Invest. Mar; 116(3):561-70.PMID: 16511588).

Although hormone therapies of administering animal-derived estrogens have been used for ameliorating menopausal disorders or the like due to such an estrogen level decline, it has been reported through the extensive randomized placebo-controlled study by the Women's Health Initiative (WHI) that such hormone therapies have potential side effects such as breast cancer, cardiovascular diseases, stroke, and blood clotting (Rossouw J E, Anderson G L, Prentice R L, et al. (2002). "Risks and benefits of estrogen plus progestin in healthy postmenopausal women: principal results From the Women's Health Initiative randomized controlled trial". JAMA 288 (3): 32133. PMID 12117397, Anderson G L, Limacher M, Assaf A R, et al. (2004). "Effects of conjugated equine estrogen in postmenopausal women with rhysterectomy: the Women's Health Initiative randomized controlled trial". JAMA 291 (14): 170112. PMID 15082697).

To this end, there is a need for the development of a substance which exhibits little or no possibility of such side effects and exerts an estrogenic effect to thereby have therapeutic effects on bone diseases, menopausal disorders, cardiovascular diseases, neurodegenerative diseases and obesity resulting from estrogen deficiency.

DISCLOSURE OF THE INVENTION

Technical Problem

Therefore, the present invention is intended to provide novel use of a substance which has little or no possibility of side effects such as cancer and exerts an estrogenic effect to thereby have therapeutic effects on bone diseases, menopausal disorders, cardiovascular diseases, neurodegenerative diseases and obesity associated with estrogen deficiency.

Technical Solution

The present inventors have surprisingly found that eupatilin represented by formula 1 below exhibits an estrogenic activity while exhibiting little or no possibility of side effects. The present invention has been completed based on these findings.

[Formula 1]

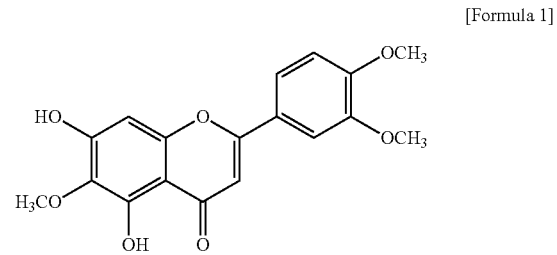 [SMILES: COc1ccc(-c2cc(=O)c3c(O)c(OC)c(O)cc3o2)cc1OC]

As used herein, the term "estrogenic activity" means an activity equal or similar to a physiological activity exhibited by estrogen which is produced in the body of a mammal including a human.

The present invention provides use of eupatilin in a medicine and/or food for treating, improving and/or preventing at least one condition selected from a bone disease, a menopausal disorder, a cardiovascular disease, a neurodegenerative disease and obesity.

Further, the present invention provides a pharmaceutical composition for treating or preventing at least one condition selected from a bone disease, a menopausal disorder, a cardiovascular disease, a neurodegenerative disease and obesity, comprising eupatilin as an active ingredient.

The eupatilin is a known compound represented by formula 1, which may be synthetic or isolated from natural products containing eupatilin and which may be domestically produced or commercially available. The eupatilin may be in the form of its pharmaceutically acceptable salt, solvate, or prodrug.

At least one condition selected from the aforementioned bone disease, menopausal disorder, cardiovascular disease, neurodegenerative disease and obesity may be due to estrogen deficiency, and the estrogen deficiency may be due to at least one selected from ovariectomy and menopause.

The bone disease may be preferably at least one condition selected from osteoporosis, osteopenia and a periodontal disease.

The cardiovascular disease may be atherosclerosis.

The neurodegenerative disease may be at least one condition selected from Parkinson's disease and Alzheimer's disease.

The treatment or prevention may be achieved by the estrogenic activity of eupatilin, and the estrogenic activity may be a selective estrogenic activity.

The selective estrogenic activity may be an activity having an estrogenic activity but selectively inhibiting cancer cell growth, and the cancer cell may be a breast cancer cell or an endometrial cancer cell.

The estrogenic activity may be achieved by the action of eupatilin as an agonist for estrogen receptor β, preferably as a tissue-selective agonist. The term "tissue-selective agonist" means that it acts as an agonist selectively depending on types of tissue.

The treatment or prevention of the bone disease may be achieved by an increase in the osteogenic activity of eupatilin.

The composition of the present invention may contain 0.1 to 99.9% by weight of the aforementioned active ingredient based on the total weight of the composition.

Further, the present invention provides a food composition for improving or preventing at least one condition selected from a bone disease, a menopausal disorder, a cardiovascular disease, a neurodegenerative disease and obesity, comprising eupatilin as an active ingredient.

Unless otherwise indicated, the same details as mentioned in the pharmaceutical composition of the present invention shall also apply to the food composition, as long as there is no contradiction therebetween. The "improving" is encompassed by the "treating" and refers to amelioration of the condition or symptoms.

The food composition may be variously included in food products including drinks, and may be present in the form of a drink, gum, tea, health functional food or the like. The health functional food may be formulated into dosage forms such as tablets, capsules, etc. The term "health functional food" as used herein refers to a food product which is manufactured (including processing, the same also applies hereinafter) using raw materials or ingredients having functionalities beneficial for humans, as defined in the Korean Health Functional Food Act No. 10219. The term "functional" as used herein means that it is taken for the purpose of controlling nutrients with respect to structures and functions of the human body or of obtaining effects beneficial for health care, such as physiological effects. The food composition may include conventional food additives. Examples of the food additives include chemical synthetic products such as ketones, glycine, sodium citrate, nicotinic acid and cinnamonic acid; natural additives such as persimmon color, licorice extract, crystalline cellulose, kaoliang color and guar gum; and compound additives such as sodium L-glutamate, alkali additives for noodles, preservatives, and tar color.

The present invention further provides a method for treating or preventing at least one condition selected from a bone disease, a menopausal disorder, a cardiovascular disease, a neurodegenerative disease and obesity, comprising administering eupatilin to a mammal in need thereof including a human. The present invention further provides use of eupatilin in the manufacture of a preparation for treating or preventing at least one condition selected from a bone disease, a menopausal disorder, a cardiovascular disease, a neurodegenerative disease and obesity. The eupatilin to be administered may be an effective amount of eupatilin.

Unless otherwise indicated, the same details as mentioned in the pharmaceutical composition of the present invention shall also apply to methods and uses of the present invention, as long as there is no contradiction therebetween.

The eupatilin or composition may be orally or parenterally administered to a mammal including a human, in the form of a suitable dosage form which is formulated by blending active ingredients in combination with pharmaceutically acceptable carriers.

Further, diluents or excipients conventionally known and used in the art, such as a filler, an extender, a binding agent, a wetting agent, a disintegrating agent and a surfactant, may be used upon the formulation of the eupatilin or composition into a desired dosage form. A solid preparation for oral administration includes a tablet, a pill, a powder, a granule, a capsule, etc., and such a solid preparation is formulated by mixing the composition of the present invention with at least one excipient such as starch, calcium carbonate, sucrose, lactose, and/or gelatin. Additionally, a lubricant such as magnesium stearate or talc may also be used. A liquid preparation for oral administration includes a suspension, a liquid for internal use, an emulsion, syrup, etc. In addition to a frequently used simple diluent such as water or liquid paraffin, the liquid preparation may contain a variety of excipients such as a wetting agent, a sweetening agent, a fragrance and/or a preservative. A preparation for parenteral administration includes an injectable solution, a suspension, an emulsion, a freeze-dried formulation, a nasal lavage fluid and a suppository. The injectable solution, suspension and emulsion may be prepared by mixing active ingredients with water, a non-aqueous solvent or a suspension solvent. Examples of the non-aqueous solvent or suspension solvent that may be used herein include propylene glycol, polyethylene glycol, vegetable oil such as olive oil, injectable ester such as ethyl oleate, or the like. As a base for the suppository, Witepsol, macrogol, Tween 61, cacao butter, laurin butter, glycerol, gelatin or the like may be used. Upon parenteral administration, subcutaneous, intravenous or intramuscular injection is possible.

Eupatilin which is included in the composition of the present invention or is used for uses and methods of the present invention may be administered once or several times at a daily dose of 0.0001 to 100 mg/kg, preferably 0.001 to 10mg/kg for adult female. However, the scope of the present invention is not limited to the above-specified dose and medication frequency.

The eupatilin may be formulated into a dosage form with addition of pharmaceutically or sitologically acceptable carriers, excipients or diluents. For example, the details of formulation into dosage forms can be found in Remington's Pharmaceutical Sciences (latest edition), Mack Publishing Company, Easton, Pa.

Advantageous Effects

The present invention enables effective treatment, improvement and/or prevention of at least one condition selected from a bone disease, a menopausal disorder, a cardiovascular disease, a neurodegenerative disease and obesity, with little or no risk of side effects such as cancer.

MODE FOR INVENTION

Figure 1:
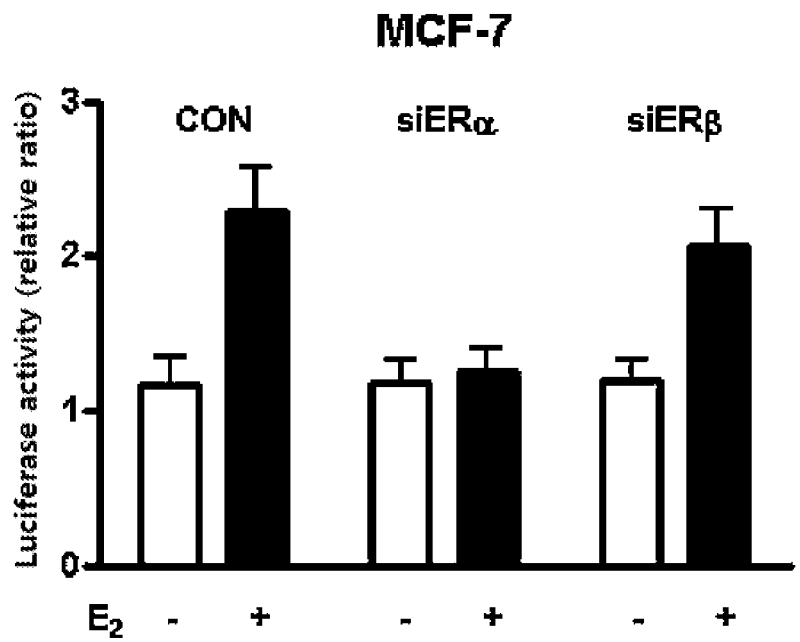
FIG. 1 is a graph showing the results of the luciferase assay for confirming effects of estrogen (E2) on breast cancer cells (MCF-7 cell line).

Now, the present invention will be described in more detail with reference to the following examples and preparation examples. These examples and preparation examples are provided only for illustrating the present invention and should not be construed as limiting the scope and spirit of the present invention.

EXAMPLE 1

Estrogenic Activity of Eupatilin

It is well known that substances with estrogenic activity are effective for bone diseases, menopausal disorders, cardiovascular diseases, neurodegenerative diseases and obesity due to estrogen deficiency (see Estrogen receptors and human disease. Deroo B J, Korach K S. J Clin Invest. 2006 March; 116(3):561-70. Review. PMID: 16511588). Therefore, by confirming through the following experiments that eupatilin displays an estrogen-like activity in a variety of estrogen-responsive cells, eupatilin was demonstrated to be effective for bone diseases, menopausal disorders, cardiovascular diseases, neurodegenerative diseases and obesity.

1-1. Preparation of Eupatilin

Eupatilin (5,7-dihydroxy-3',4',6-trimethoxyflavone; CAS Registry Number: 22368-21-4), which had been prepared from *Artemisia princes* using known processes of isolation, purification, and confirmation of the structure and purity (see Inhibitory effect of eupatilin and jaceosidin isolated from *Artemisia princeps* on carrageenan-induced inflammation in mice. J Ethnopharmacol. 2009 Sep. 25; 125(3):497-500; etc.), was provided by courtesy of Prof. Dr. Baek, Nam-In (Kyung Hee University, South Korea). Specifically, *Artemisia princes* Pampanini collected in the field of GangHwa-Do, South Korea was deposited as a voucher specimen (KHU05067) with the Natural Products Chemistry Laboratory at Kyung Hee University. The same kind of *Artemisia princeps* Pampanini as the deposited specimen was extracted with 80% ethanol, evaporated under reduced pressure, suspended in water and then extracted with ethyl acetate (EtOAc). The ethyl acetate fraction was chromatographed on silica gel (4 cm×20 cm) eluting with a stepwise gradient of n-hexane and EtOAc (7:1, 5:1, 3:1, 1:1, v/v) to give 20 fractions (SSE-1 to SSE-20). Fraction 16 (SSE-16) was subjected to re-fractionation using a solvent pair of $CHCl_3$-MeOH (30:1, v/v) to afford Compound 1 (SSE-16-4). Compound 1 was identified to be eupatilin, based on physicochemical properties, spectroscopic analysis, and comparison with the results of literature. The purity was analyzed using a HPLC system (Young Lin Instrument Co., Ltd., South Korea) and was more than 95%. Eupatilin: yellowish powder. mp 226-228° C.; IR (KBr, $cm^{-1}$) 3390, 3266, 1655, 1514; EI-MS m/z (70 eV): 344 [$M^+$]

1-2. Preparation of Cells

MCF-7 (estrogen receptor-positive human breast cancer cell line), Ishikawa (estrogen receptor-positive endometrial cancer cell line), and MG-63 (human osteosarcoma; osteoblast-like cell line) were obtained from the American Type Culture Collection (ATCC). BG-1 (uterine cancer cell line) was furnished by courtesy of Dr. Korach (NIH, USA). Cells were cultured in a Dulbecco's modified Eagle's medium (DMEM) containing 10% fetal bovine serum (FBS), 100 U/ml penicillin and 100 U/ml streptomycin, at 37° C. and 5% $CO_2$.

1-3. Luciferase Assay

The luciferase assay is an assay of estimating an estrogenic activity by measuring the degree of a luciferase activity generated upon binding of a substance having an estrogenic activity to an estrogen receptor. This assay was carried out in the following procedure. Unless otherwise specified, the reagents used were purchased from Gibco (Karlwruhe, Germany).

The luciferase reporter plasmid used was 3×ERE TATA luc. (Addgene, Cambridge, USA). In order to control transfection efficiency, phRenilla-luciferase-CMV (Promega, Mannheim, Germany) as an internal control plasmid was co-transfected. Cells were cultured at a density of $2 \times 10^5$ cells/well in a 6-well plate, in a phenol red-free DMEM (Dulbecco's modified Eagle's medium) supplemented with 100 U/ml penicillin, 100 mg/ml streptomycin, 1 mM sodium pyruvate, 1 mM glutamine, and 10% charcoal dextran-treated fetal bovine serum (FBS). After the cells were cultured to a 50 to 60% confluence, the medium was removed, the cells were placed at 37° C. and 5% $CO_2$ for 6 hours on a serum-free OPTI-MEM medium containing plasmid DNA constructs and 2 μg/ml of polyethyleneimine (PEI), according to the manufacturer's instructions. 1 μg/well of 3×ERE TATA luc and 100 ng of a phRL-CMV plasmid were subjected to transfection.

After the period of transfection, the medium was replaced with a phenol-free DMEM supplemented with 10% charcoal dextran-treated FBS, and the cells were cultured at 37° C. and 5% $CO_2$ overnight prior to treatment of eupatilin.

After 18 hours of culture, the medium was replaced with a eupatilin-containing medium. The proteins were extracted 24 hours later, and firefly and renilla luciferase activities were measured on a luminometer (Molecular Devices, Sunnyvale, Calif.) using a Dual Luciferase Assay kit (Promega, Madison, Wis.) according to the manufacturer's instructions.

All experiments were carried out in triplicate and were repeated at least three times. For the luciferase assay, total cell lysates were prepared, the firefly luciferase activity was assayed and normalized to the renilla luciferase activity according to the manufacturer's instructions (Promega). Further, in order to knock down the cell levels of specific proteins, cells with co-transfection of small interfering RNAs (siRNAs) together with 3×ERE TATA luc and phRL-CMV were prepared and subjected to the same treatment of eupatilin or the like as in the cells which were not treated with siRNAs. The siRNAs used were purchased from Bioneer Corporation (Daejeon, South Korea) and treated at a concentration of 50 nM. The "siERα" means siRNA which inhibits the expression of ERα, and the "siERβ" means siRNA which inhibits the expression of ERβ.

For comparative purposes, a group treated with estrogen, i.e., 17-β-estradiol (hereinafter, referred to simply as "E2") in place of eupatilin was taken as a comparative group, and a non-treated group subjected to the same treatment as in the eupatilin-treated group, except that there was no treatment with eupatilin or E2, was served as control.

Treatment concentrations of eupatilin and E2 are shown in the following tables, in which the luciferase activity is given in terms of a relative fold activity, given that the luciferase activity for the non-treated group is 1 as a baseline.

The luciferase assay results for various types of cells are given in the following tables. Table 1 shows the results for MCF7 cell line, Table 2 shows the results for BG-1 cell line, Table 3 shows the results for Ishikawa cells, and Table 4 shows the results for MG63 cell line.

TABLE 1

| | Group (conc.) | | | | |
|---|---|---|---|---|---|
| | Not treated (0) | E2 treated ($10^{-7}$ M) | Eupatilin treated (0.01 µg/ml) | Eupatilin treated (0.1 µg/ml) | Eupatilin treated (1 µg/ml) |
| Luciferase activity (-fold) | 1.0 | 2.8 | 2.4 | 2.3 | 2.8 |

TABLE 2

| | Group (conc.) | | | | |
|---|---|---|---|---|---|
| | Not treated (0) | E2 treated ($10^{-7}$ M) | Eupatilin treated (0.01 µg/ml) | Eupatilin treated (0.1 µg/ml) | Eupatilin treated (1 µg/ml) |
| Luciferase activity (-fold) | 1.0 | 4.1 | 2.9 | 3.3 | 3.7 |

TABLE 3

| | Group (conc.) | | | | |
|---|---|---|---|---|---|
| | Not treated (0) | E2 treated ($10^{-7}$ M) | Eupatilin treated (0.01 µg/ml) | Eupatilin treated (0.1 µg/ml) | Eupatilin treated (1 µg/ml) |
| Luciferase activity (-fold) | 1.0 | 2.1 | 1.4 | 1.9 | 2.9 |

TABLE 4

| | Group (conc.) | | | | |
|---|---|---|---|---|---|
| | Not treated (0) | E2 treated ($10^{-7}$ M) | Eupatilin treated (0.01 µg/ml) | Eupatilin treated (0.1 µg/ml) | Eupatilin treated (1 µg/ml) |
| Luciferase activity (-fold) | 1.0 | 1.5 | 2.1 | 1.7 | 1.6 |

As shown from the results of Tables 1 to 4, eupatilin exhibited an activity similar to that of estrogen, i.e., estradiol (E2), in a variety of estrogen-responsive cells, i.e., breast cancer cells, uterine cancer cells, endometrial cancer cells, and osteoblasts.

From these results, it is demonstrated that eupatilin exhibiting an estrogenic activity is effective for the treatment, improvement and/or prevention of bone diseases, menopausal disorders, cardiovascular diseases, neurodegenerative diseases or obesity which may be caused by estrogen deficiency.

EXAMPLE 2

Side Effect Inhibitory Effects by Selective Estrogenic Activity of Eupatilin

The following experiments were carried out to verify inhibitory effects of eupatilin on cancer or the like which is a side effect that may be produced upon application of conventional animal-derived substances with estrogenic activity.

2-1. Cancer Cell Growth Inhibitory Effects

Cell viability was estimated by the MTT (3-[4,5-dimethylthiazol-2-yl]-2,5-diphenyltetrazolium bromide; Sigma-Aldrich) assay to confirm cancer cell growth inhibitory effects of eupatilin.

MCF7 breast cancer cells were seeded onto a 96-well plate and incubated for 24 hours. The cells were treated with $10^{-8}$ M or $10^{-7}$ M E2 or with 0.1 µg/ml or 1 µg/ml of eupatilin for 48 hours. On the day of collection, 50 µl of MTT solution (5 mg/ml in PBS) was added to the medium, followed by incubation at 37° C. for 4 hours. The MTT-containing medium was removed and the cells were solubilized in DMSO (100 µl) for 30 min. The cell viability was determined in terms of an optical density at 540 nm using a microplate spectrophotometer (SpectraMax; Molecular Devices, Sunnyvale, Calif.).

Ethanol which is a vehicle was served as control for the E2-treated group, and DMSO was served as control for the eupatilin-treated group.

The viability is expressed in terms of a relative ratio by taking a value of the control to be 100, and the lethality is also expressed in terms of a relative ratio by taking a value of the control to be 100.

The results are given in the following tables. Table 5 shows the results confirming the viability of the breast cancer cell line when treated with estrogen (E2), and Table 6 shows the results confirming the lethality of the breast cancer cell line when treated with eupatilin.

TABLE 5

| | Group (conc.) | | |
|---|---|---|---|
| | Not treated (0) | E2 treated ($10^{-8}$ M) | E2 treated ($10^{-7}$ M) |
| Cell viability (% relative to control) | 0 | 18.5 | 21.4 |

TABLE 6

| | Group (conc.) | | |
|---|---|---|---|
| | Not treated (0) | Eupatilin treated (0.1 µg/ml) | Eupatilin treated (1 µg/ml) |
| Cell lethality (% relative to control) | 0 | 21.5 | 24.5 |

2-2. Cancer Cell Growth Inhibition Mechanism

Utilizing the results for siRNA-treated cancer cells obtained in the luciferase assay conducted in Section 1-3, an attempt was made to elucidate the cancer cell growth inhibition mechanism by confirming effects of eupatilin on cancer cells in which expression of ERα was inhibited by treatment of siERα or cancer cells in which expression of ERβ was inhibited by treatment of siERβ. "E2" is for being treated at a concentration of $10^{-7}$ M, and "Eupatilin" is for being treated at a concentration of 0.1 or 1.0 µg/ml.

The results obtained are shown in FIGS. 1 to 4.

Figure 2:
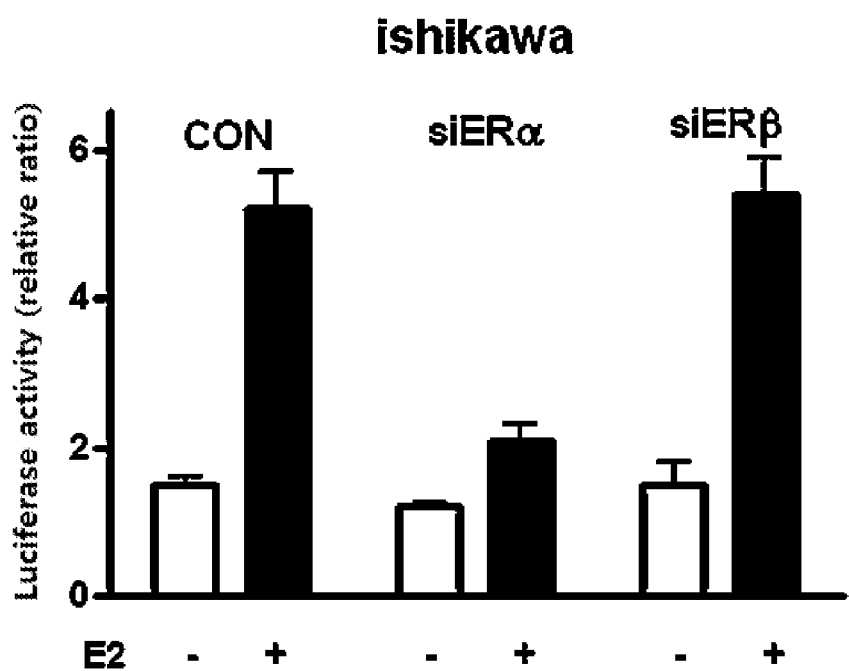
FIG. 2 is a graph showing the results of the luciferase assay for confirming effects of estrogen (E2) on endometrial cancer cells (Ishikawa cell line).
Figure 3:
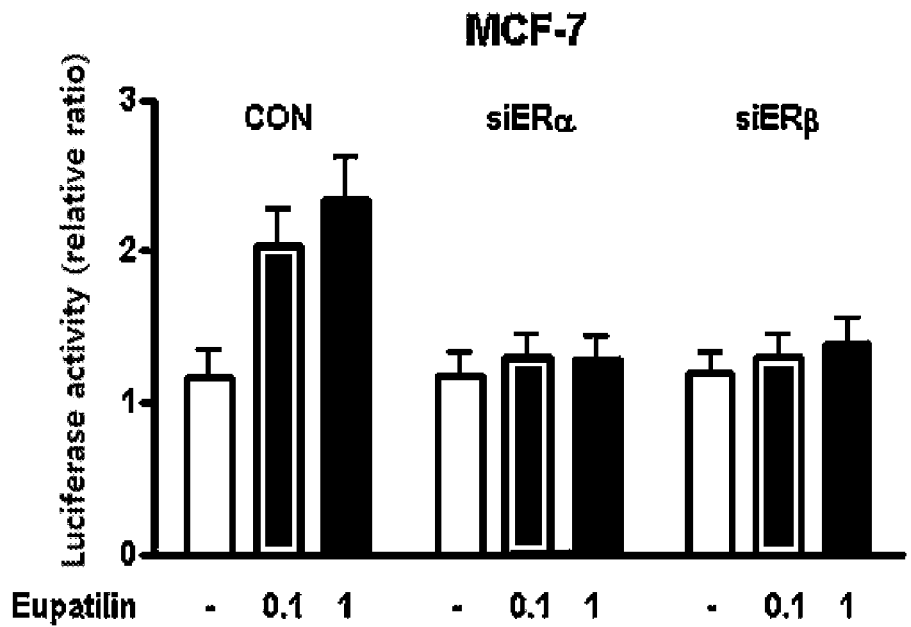
FIG. 3 is a graph showing the results of the luciferase assay for confirming effects of eupatilin on breast cancer cells (MCF-7 cell line).
Figure 4:
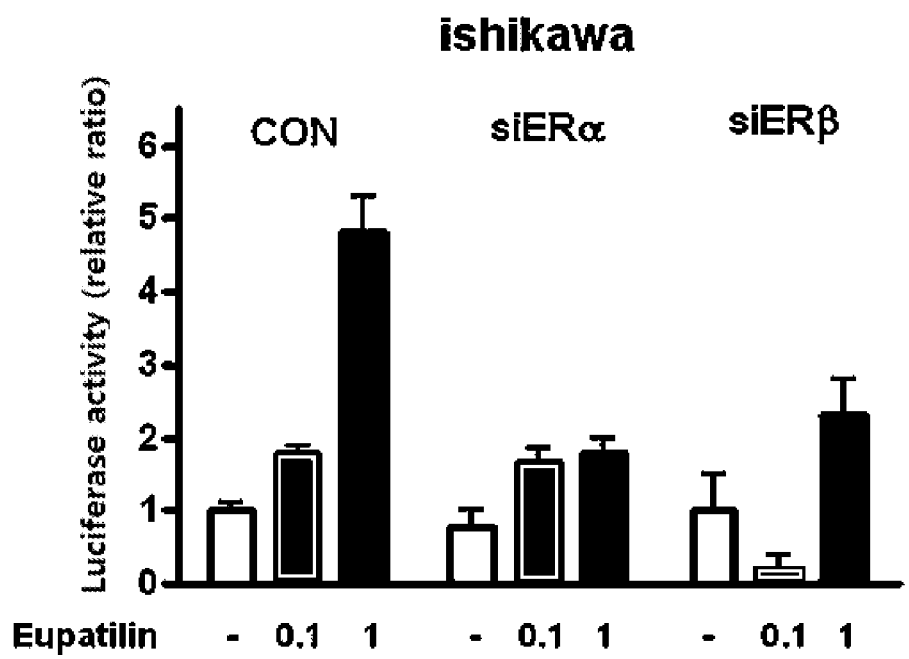
FIG. 4 is a graph showing the results of the luciferase assay for confirming effects of eupatilin on endometrial cancer cells (Ishikawa cell line).

FIG. 1 illustrates the results for treatment of estrogen (E2) on breast cancer cells (MCF-7 cell line), FIG. 2 illustrates the results for treatment of estrogen (E2) on endometrial cancer cells (Ishikawa cell line), FIG. 3 illustrates the results for treatment of eupatilin on breast cancer cells (MCF-7 cell line), and FIG. 4 illustrates the results for treatment of eupatilin on endometrial cancer cells (Ishikawa cell line). Referring to FIGS. 1 to 4, "CON" represents a non-siRNA treated group, "siERα" represents a group treated with siRNA which inhibits ERα expression, and "siERβ" represents a group treated with siRNA which inhibits ERβ expression. Additionally, referring to FIGS. 1 and 2, "−" means "E2 not treated" and "+" means "E2 treated", and referring to FIGS. 3 and 4, "−" means "eupatilin not treated", and each of "0.1" and "1" means "treated with 0.1 µg/ml of eupatilin" or "treated with 1.0 µg/ml of eupatilin".

As shown in FIGS. 1 to 4, it can be seen that estrogen (E2) largely induces cell proliferation via only ERα as a cell growth factor, in breast cancer cells and endometrial cancer cells, whereas eupatilin acts equally on both ERα and ERβ. That is, it can be seen that, in addition to as an agonist for estrogen receptor α, eupatilin also acts as an agonist for estrogen receptor β in cancer cells.

From the results of Sections 2-1 and 2-2, it can be seen that eupatilin inhibits, unlike estradiol, cancer cell growth, this is because estradiol acts largely on only ERα, whereas eupatilin acts also on ERβ in breast cancer cells and endometrial cancer cells, which inhibits ERα-mediated effects to suppress the proliferation of cancer cells. This has also been supported by previous study results (see Deroo B J, Korach K S. (2006) "Estrogen receptors and human disease" J Clin Invest. March; 116(3):561-70.PMID: 16511588).

Accordingly, it is demonstrated that eupatilin has a little or lower possibility of inducing cancer such as breast cancer or endometrial cancer and, on the contrary, inhibits the occurrence of such cancer to thereby result in no or lower risk of side effects exhibited by estrogen such as estradiol.

EXAMPLE 3

Bone Loss Inhibitory Effect of Eupatilin

By confirming that eupatilin has an effect of increasing a bone density in osteoblastic cells, effectiveness of eupatilin for bone diseases associated with estrogen deficiency, such as osteoporosis, osteopenia or periodontal diseases, was demonstrated in the following manner.

3-1. Bone Density-Increasing Effect of Eupatilin in Osteoblastic Cells

The ALP activity in MG-63 cells treated with eupatilin was measured to confirm that eupatilin enhances a bone density in osteoblastic cells. Since osteoblasts specifically exhibit an alkaline phosphatase (ALP) activity when undergoing cell differentiation, measurement of the ALP activity makes it possible to confirm cell differentiation and differentiation degree of osteoblasts. Based on the fact that ALP degrades p-nitrophenylphosphate into p-nitrophenol and phosphate, effects of eupatilin on osteoblasts were observed by measuring an ALP activity in terms of an absorbance ratio between the absorbance of each substance and the absorbance of the control at 405 nm.

Specifically, MG-63 cells were seeded and stabilized for 18 hours, and thereafter E2 was treated at a concentration of $10^{-7}$ M, whereas eupatilin was treated at a concentration of 0.2 or 2.0 µg/ml. After 24 hours of the treatment, lysates were prepared and slowly shaken for 30 min. Then, the ALP activity was assayed by measuring the release of p-nitrophenol from p-nitrophenylphosphate (20 mM in 1M diethanolamine buffer supplemented with $MgCl_2$ at pH 9.8). The absorbance was measured at 405 nm. The standard curve was drawn using various concentrations of bovine serum albumin (BSA; Sigma) within the range of 0 to 0.1 U/ml PBS-T. The ALP values were adjusted for the protein content of the corresponding cell lysates. The cultures protein content was quantified by means of a bicinchoninic acid protein assay (Thermo Scientific). The results obtained were compared with those of the control to which only BSA was added at a concentration of 100 nM and no specimen was added.

The results are given in Table 7 below. Table 7 shows the results confirming effects of eupatilin on ALP activity in the MG-63 cell line.

TABLE 7

| | Group (conc.) | | | |
|---|---|---|---|---|
| | Not treated (0) | E2 treated ($10^{-7}$ M) | Eupatilin treated (0.2 µg/ml) | Eupatilin treated (2.0 µg/ml) |
| ALP activity (% relative to control) | 0 | 18.1 | 20.5 | 60 |

As shown in Table 7, it can be seen that eupatilin, similar to estrogen (E2), increases an ALP activity in osteoblastic cells and the activity is increased in a dose-dependent manner.

An increased ALP activity in osteoblastic cells indicates active differentiation of osteoblasts. Thus, it is demonstrated that eupatilin is effective for estrogen deficiency-related bone diseases such as osteoporosis, osteopenia or periodontal diseases.

3-2. Bone Density-Increasing Mechanism of Eupatilin in Osteoblastic Cells

Utilizing the results for siRNA-treated MG-63 cells obtained in the luciferase assay conducted in Section 1-3, an attempt was made to elucidate the mechanism by confirming effects of eupatilin on osteoblastic cells in which expression of ERα was inhibited by treatment of siERα or osteoblastic cells in which expression of ERβ was inhibited by treatment of siERβ. "E2" is for being treated at a concentration of $10^{-7}$ M, and "Eupatilin" is for being treated at a concentration of 0.1 or 1.0 µg/ml.

Figure 5:
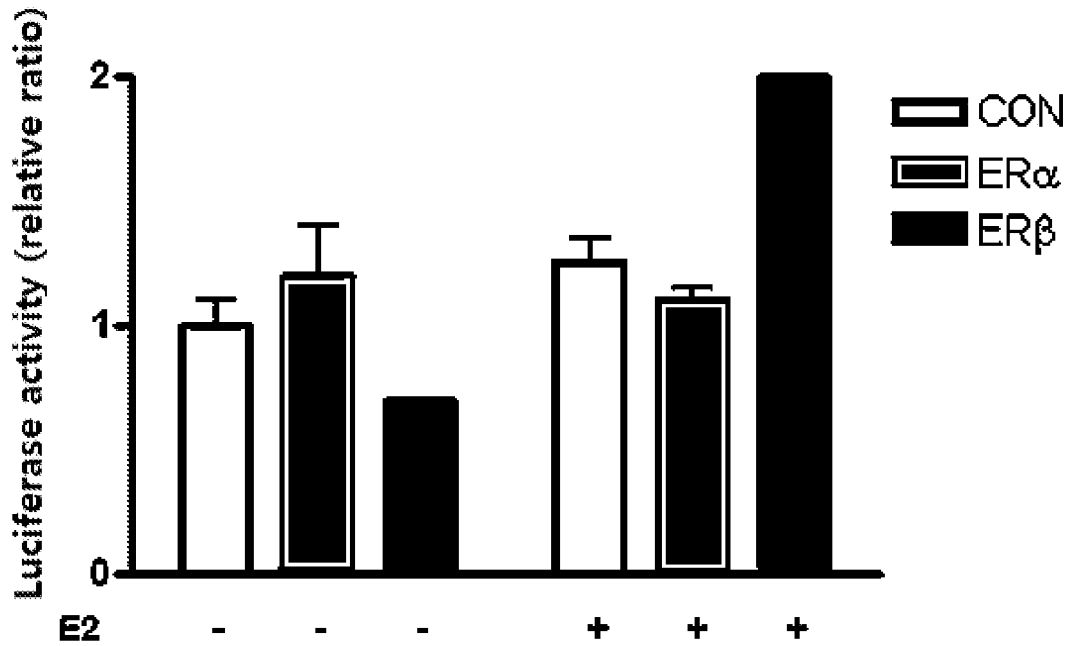
FIG. 5 is a graph showing the results of the luciferase assay for confirming effects of estrogen on osteoblastic cells.
Figure 6:
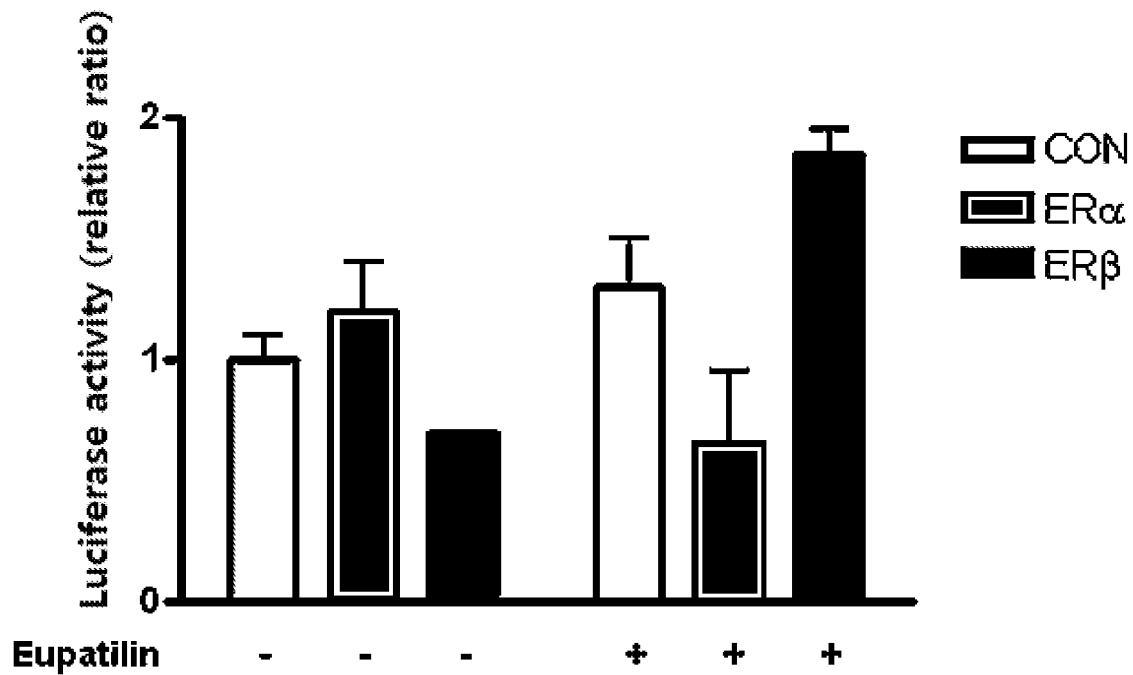
FIG. 6 is a graph showing the results of the luciferase assay for confirming effects of eupatilin on osteoblastic cells.

The results obtained are shown in FIGS. 5 and 6. FIG. 5 illustrates the results for treatment with estrogen (E2), and FIG. 6 illustrates the results for treatment with eupatilin. Referring to FIGS. 5 and 6, "CON" represents a non-siRNA treated group, "siERα" represents a group treated with siRNA which inhibits ERα expression, and "siERβ" represents a group treated with siRNA which inhibits ERβ expression. Additionally, referring to FIG. 5, "−" means "E2 not treated" and "+" means "E2 treated", and referring to FIG. 6, "−" means "eupatilin not treated", and "+" means "eupatilin treated".

As shown in FIGS. 5 and 6, it can be seen that eupatilin also acts selectively on ERβ, similar to that estrogen (E2) acts selectively on ERβ in osteoblastic cells. Based on the fact that estrogen (E2) acts selectively on ERβ to increase a bone density in osteoblastic cells (see Medicarpin, a legume phytoalexin, stimulates osteoblast differentiation and promotes peak bone mass achievement in rats: evidence for estrogen receptor β-mediated osteogenic action of medicarpin, J Nutr Biochem. 2011, PMID: 21333515; Estrogen receptor-beta modulates synthesis of bone matrix proteins in human osteoblast-like MG63 cells. J Cell Biochem. 2003 PMID: 12682916), it can be seen that eupatilin also acts selectively on ERβ to enhance a bone density in osteoblastic cells. That is, it can be seen that eupatilin acts as an agonist for estrogen receptor β in osteoblastic cells, and serves as an organ-selective agonist which selectively acts particularly in organs such as bone.

From the results of Sections 3-1 and 3-2 above, it is demonstrated that eupatilin, like estrogen (E2), acts selectively on ERβ in osteoblastic cells to increase a bone density in osteoblastic cells.

Therefore, it can be seen that eupatilin is effective for estrogen deficiency-related bone diseases such as osteoporosis, osteopenia or periodontal diseases.

As a result, it can be seen that, as reviewed in Examples 1 to 3, eupatilin functions in an organ-selective manner and is therefore effective for bone diseases while producing little or no risk of side effects exhibited by estrogen such as estradiol.

Accordingly, it is demonstrated that eupatilin is effective for the treatment, improvement and/or prevention of at least one condition selected from bone diseases including osteoporosis, osteopenia or periodontal diseases, menopausal disorders, cardiovascular diseases including atherosclerosis, neurodegenerative diseases including Parkinson's disease and Alzheimer's disease, and obesity.

PREPARATION EXAMPLE 1

Manufacture of Pharmaceutical Composition 300 mg of eupatilin prepared in the same manner as in Example 1-1, 100 mg of corn starch, 100 mg of lactose, and 2 mg of magnesium stearate were filled in a gelatin capsule to give a capsule.

PREPARATION EXAMPLE 2

Manufacture of Food Composition

Eupatilin (4% by weight) prepared in the same manner as in Example 1-1, liquid fructose (0.5% by weight), oligosaccharide (2% by weight), sugar (2% by weight), salt (0.5% by weight) and a balance of water were homogeneously mixed and flash pasteurized to prepare a health drink.

INDUSTRIAL APPLICABILITY

The present invention is capable of providing effective treatment, improvement and/or prevention of at least one condition selected from bone diseases, menopausal disorders, cardiovascular diseases, neurodegenerative diseases and obesity while producing little or no possibility of side effects such as cancer, and is therefore industrially applicable.

What is claimed is:

1. A method for treating hot flashes, wherein the hot flashes are caused by estrogen deficiency, comprising administering an effective amount of eupatilin to a mammal in need thereof, wherein the treatment is achieved by estrogenic activity of eupatilin.

2. A method for treating hot flashes, comprising administering an effective amount of eupatilin to a mammal in need thereof, wherein the treatment is achieved by estrogenic activity of eupatilin, wherein the estrogenic activity is a selective estrogenic activity.

3. A method for treating hot flashes, comprising administering an effective amount of eupatilin to a mammal in need thereof, wherein the treatment is achieved by estrogenic activity of eupatilin, wherein the estrogenic activity is achieved by eupatilin acting as an agonist for estrogen receptor β.

* * * * *